(12) United States Patent
Omura et al.

(10) Patent No.: US 8,182,828 B2
(45) Date of Patent: May 22, 2012

(54) OIL-IN-WATER EMULSIFIED MILKY SKIN COSMETIC PREPARATION

(75) Inventors: Takayuki Omura, Yokohama (JP); Yuko Matsui, Yokohama (JP)

(73) Assignee: Shiseido Company Ltd., Chuo-ku, Tokyo (JP)

( * ) Notice: Subject to any disclaimer, the term of this patent is extended or adjusted under 35 U.S.C. 154(b) by 198 days.

(21) Appl. No.: 12/369,929

(22) Filed: Feb. 12, 2009

(65) Prior Publication Data
US 2009/0202600 A1   Aug. 13, 2009

(30) Foreign Application Priority Data
Feb. 13, 2008   (JP) .................................. 2008-32354

(51) Int. Cl.
*A61K 8/03* (2006.01)
(52) U.S. Cl. ........................................................ 424/401
(58) Field of Classification Search ................... None
See application file for complete search history.

(56) References Cited

U.S. PATENT DOCUMENTS

| 2004/0234477 A1* | 11/2004 | Sakuta ..................... 424/70.12 |
| 2005/0053568 A1 | 3/2005 | Aubrun-Sonneville et al. |
| 2007/0134265 A1 | 6/2007 | Takada et al. |

FOREIGN PATENT DOCUMENTS

| EP | 1437118 A1 | 7/2004 |
| JP | 2521467 | 5/1996 |
| JP | 2003-95845 | 4/2003 |
| JP | 2004-315525 | 11/2004 |
| JP | 2005-336095 | 12/2005 |
| JP | 2007-238521 | 9/2007 |

OTHER PUBLICATIONS

Japanese Patent Abstract Publication No. 2007-238521 published Sep. 20, 2007, 17 pages.
European Search Report for corresponding EP 09152653 mailed Jul. 22, 2009, four pages.
Japanese Patent Abstract for Publication No. 63-264512 published Nov. 1, 1988, one page.
Japanese Patent Abstract for Publication No. 2003-095845 published Apr. 3, 2003, eight pages.
Japanese Patent Abstract for Publication No. 2005-336095 published Dec. 8, 2005, 19 pages.

* cited by examiner

*Primary Examiner* — Tracy Vivlemore
*Assistant Examiner* — Jennifer Berrios
(74) *Attorney, Agent, or Firm* — Rankin, Hill & Clark LLP

(57) ABSTRACT

The present invention provides an oil-in-water emulsified milky skin cosmetic preparation, which is able to impart a refreshing feeling, an astringent effect, a moisturizing effect, and a softening effect to skin, when it is singly used, and which is excellent in terms of emulsion stability although it has a high water content and a low viscosity, presenting a milk white color. An oil-in-water emulsified milky skin cosmetic preparation comprising (a) a copolymer of 2-acrylamide 2-methylpropanesulfonic acid or a salt thereof/polyoxyethylene alkyl ether methacrylate, (b) an alkyl modified carboxyvinyl polymer; and (c) an alkylene oxide derivative, and having a viscosity at 25° C. of 10,000 mPa·s or less (Vismetron viscometer). It is preferable that the skin cosmetic preparation comprises 0.005% to 2.0% by mass of (a), 0.005% to 1.5% by mass of (b), and 0.005% to 15.0% by mass of (c). The skin cosmetic preparation may further comprise (d) oil having a viscosity at 25° C. of 100 mPa·s or less and being a liquid at an ordinary temperature, arbitrarily. Furthermore, it is preferable that the skin cosmetic preparation comprises 55% to 80% by mass of water.

5 Claims, No Drawings

OIL-IN-WATER EMULSIFIED MILKY SKIN COSMETIC PREPARATION

RELATED APPLICATIONS

This application claims the priority of Japanese Patent Application No. 2008-32354 filed on Feb. 13, 2008, which are incorporated herein by reference.

FIELD OF THE INVENTION

The present invention relates to an oil-in-water emulsified milky skin cosmetic preparation. The present invention particularly relates to an oil-in-water emulsified milky skin cosmetic preparation, which is produced for integration of a skin lotion with a skin milk, and is excellent in terms of the feeling of use (dewy feeling, no stickiness, refreshing and emollient feeling, etc. when applied) and preservation stability.

BACKGROUND OF THE INVENTION

In general, a skin lotion is used for hydrate skin and providing moisturizing ingredient to skin, so as to keep fresh, radiant and smooth skin filled with water. In addition, a lotion exhibiting an astringent effect and the effect of suppressing sebum secretion is essential as a basic skin care product. Ingredients mixed into such a skin lotion include: water; lower alcohols such as ethanol; moisturizers such as glycerin, propylene glycol, dipropylene glycol, or 1,3-butylene glycol; softening agents or emollient agents comprising vegetable oils such as ester oil, olive oil, or jojoba oil; solubilizers that are surfactants having a high HLB value; buffers used for the pH control of the cosmetic preparation or the pH balance of the skin, such as citric acid or lactic acid; thickeners used for the improvement of the feeling of use or for ensuring stability; aromatics; antiseptics; and other ingredients. In order to impart moisturizing and softening effects required for skin milk to a skin lotion comprising the aforementioned ingredients, if the mixed amount of a moisturizer or oil of skin lotion is increased, it causes problems of separation and so on.

On the other hand, in order to keep the moisture balance of skin, a skin milk mainly comprises water, a moisturizer, and oil. Thus, a skin milk has been widely used as a basic skin care product for giving moisture and softness to the skin. In order to impart a refreshing feeling or dewy feeling, which is generally achieved by the aforementioned skin lotion, to the skin milk, if the mixed amount of water or ethanol is increased to the skin milk, it also causes problems of separation or the like.

Thus, for reason of product stability, a skin lotion and a skin milk have generally been used separately. However, recently a cosmetic preparation has been proposed for obtaining the feeling of use of a skin lotion and that of a skin milk by a single product (see Japanese patent No. 2521467 and Japanese patent publication of unexamined application No. 2003-95845, for example). However, in the case of the cosmetic preparations described in the aforementioned documents, the mixed amount of oil is relatively small in terms of stability, and these cosmetic preparations are translucent. As a visual effect obtained from the appearance of a cosmetic product, the white color of a common skin milk brings on creaminess of the products. This contributes to the improvement of a satisfaction level when the skin milk is applied. Moreover, with regard to the feeling of use as a skin lotion, it is desired for a skin lotion to have watery texture, that is, to be a cosmetic preparation containing relatively large amount of water and showing a low viscosity. To date, it has been difficult to prepare a milky white skin cosmetic preparation, which is a single product and having both of the feeling of use of a skin lotion and that of a skin milk, and which has excellent stability even when it has a high water content and a low viscosity.

It is to be noted that Japanese patent publication of unexamined application No. 2004-315525 and Japanese patent publication of unexamined application No. 2005-336095, which are publications regarding prior art techniques, describe that ingredient (a) used in the present invention or a polymer similar thereto is mixed into a cosmetic preparation.

[Patent Literature 1] Japanese patent No. 2521467
[Patent Literature 2] Japanese patent publication of unexamined application No. 2003-95845
[Patent Literature 3] Japanese patent publication of unexamined application No. 2004-315525
[Patent Literature 4] Japanese patent publication of unexamined application No. 2005-336095

DISCLOSURE OF THE INVENTION

Problem to be Solved by the Invention

If a skin lotion having high effects is combined with a skin milk having high effects to produce a single cosmetic preparation, it becomes easy to apply the cosmetic preparation onto the skin, and it leads to save users' skin care steps. Accordingly, the development of a milky white cosmetic preparation, which is capable of playing both roles as a skin lotion and a skin milk and which has excellent stability even when it has a high water content and a low viscosity, has been considered a big challenge for researchers.

Means to Solve the Problem

The present inventors have found that a specific copolymer, an alkyl modified carboxyvinyl polymer, and a specific alkylene oxide derivative are combined, so as to obtain an oil-in-water emulsified milky skin cosmetic preparation, which achieves a single cosmetic preparation being integrated a skin lotion with a skin milk, has an excellent feeling of use (dewy feeling, no stickiness, refreshing and emollient feeling, etc. when applied), and is excellent in stability with milky white color although it has a high water content and a low viscosity, thereby completing the present invention.

Specifically, the present invention provides an oil-in-water emulsified milky skin cosmetic preparation, which comprises the following ingredient (a), ingredient (b) and ingredient (c), and which has a viscosity at 25° C. of 10,000 mPa·s or less (Vismetron viscometer), ingredient (a): a 2-acrylamide-2 methylpropanesulfonic acid or a salt thereof/polyoxyethylene alkyl ether methacrylate copolymer represented by the following formula (I):

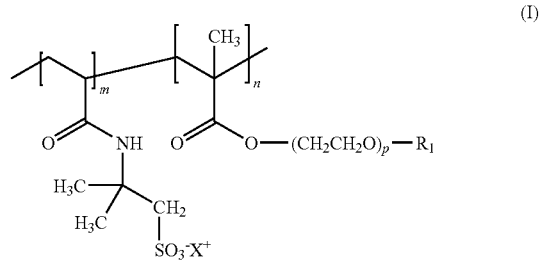

wherein each of m, n and p represents an average number of moles added, and m/n=4 to 99 and p represents an integer of 10 to 50; $X^+$ represents a proton, an alkaline metal cation, an alkaline-earth metal cation, ammonium ion, or an organic cation; $R_1$ represents a hydrogen atom, or a linear or branched alkyl group containing 5 to 40 carbon atoms;

ingredient (b): an alkyl modified carboxyvinyl polymer; and ingredient (c): an alkylene oxide derivative represented by the following formula (II):

$$R_2O\text{-}[(AO)_a(EO)_b]\text{—}R_3 \qquad (II)$$

wherein AO represents an oxyalkylene group containing 3 or 4 carbon atoms; EO represents an oxyethylene group; each of a and b is an average number of moles added of the AO and EO, respectively, and $1 \leq a \leq 70$ and $1 \leq b \leq 70$; the percentage of EO to the sum of AO and EO [EO/(AO+EO)] is 20% to 80% by mass; and each of $R_2$ and $R_3$ independently represents an alkyl group containing 1 to 4 carbon atoms.

In addition, the present invention provides the oil-in-water emulsified milky skin cosmetic preparation, which comprises 0.005% to 2.0% by mass of the ingredient (a), 0.005% to 1.5% by mass of the ingredient (b), and 0.005% to 15.0% by mass of the ingredient (c).

Moreover, the present invention provides the oil-in-water emulsified milky skin cosmetic preparation, which further comprises, as ingredient (d), oil that has a viscosity at 25° C. of 100 mPa·s or less and is a liquid at an ordinary temperature.

Furthermore, the present invention provides the oil-in-water emulsified milky skin cosmetic preparation, which comprises 1.0% to 10.0% by mass of the ingredient (d).

Furthermore, the present invention provides the oil-in-water emulsified milky skin cosmetic preparation, which comprises 55% to 80% by mass of water.

Effect of the Invention

The present invention provides an oil-in-water emulsified milky skin cosmetic preparation, which is able to impart a refreshing feeling, an astringent effect, a moisturizing effect, and a softening effect to skin, when it is singly used, and which is excellent in terms of emulsion stability though it has a low viscosity presenting a milk white color.

DETAILED DESCRIPTION OF THE PREFERRED EMBODIMENT

The oil-in-water emulsified milky skin cosmetic preparation of the present invention will be described in detail below.

The ingredient (a) of the skin cosmetic preparation of the present invention is a 2-acrylamide-2 methylpropanesulfonic acid or a salt thereof/polyoxyethylene alkyl ether methacrylate copolymer represented by the following formula (I):

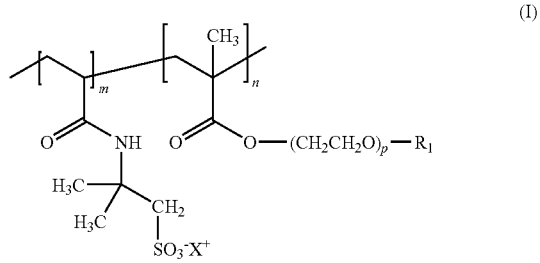

In the above formula (I), each substituent and each symbol have the following meanings.

Each of m, n and p represents an average number of moles added. The symbol m indicates a value, whereby 2-acrylamide-2 methylpropanesulfonic acid or a salt thereof becomes 80 mol % to 99 mol % in the copolymer represented by the formula (I). The symbol n indicates a value, whereby polyoxyethylene alkyl ether methacrylate becomes 1 mol % to 20 mol % in the copolymer represented by the formula (I). If such m and n are expressed in the form of m/n (ratio), m/n=4 to 99. When the m/n ratio is less than 4, namely, when the ratio of polyoxyethylene alkyl ether methacrylate to 2-acrylamide-2 methylpropanesulfonic acid or a salt thereof in the copolymer represented by the formula (I) exceeds the aforementioned range, the obtained oil-in-water emulsified milky skin cosmetic preparation becomes excellent in terms of the emulsifying property of oil, but it becomes poor in terms of the viscosity as a skin cosmetic preparation. Thus, it is not preferable. On the other hand, when the m/n ratio becomes greater than 99, namely, when the ratio of 2-acrylamide-2 methylpropanesulfonic acid or a salt thereof to polyoxyethylene alkyl ether methacrylate in the copolymer represented by the formula (I) exceeds the aforementioned range, the obtained oil-in-water emulsified milky skin cosmetic preparation becomes poor in terms of the emulsifying property of oil, and thus, a stable emulsified composition cannot be obtained.

The symbol p represents an average number of moles of ethylene oxide added to the copolymer represented by the formula (I). In the present invention, such p represents an integer of 10 to 50, preferably 15 to 45, and more preferably 20 to 30. If the p value is less than 10, the obtained oil-in-water emulsified skin cosmetic preparation is poor in terms of the emulsifying property of oil. In contrast, if the above value exceeds 50, stickiness is felt when applied.

$X^+$ represents a proton, an alkaline metal cation (for example, $Na^+$, $K^+$, etc.), an alkaline-earth metal cation (for example, $Ca^{++}$, $Mg^{++}$, etc.), ammonium ion ($NH_4^+$), or an organic cation (for example, n-alkylammonium ion, n-alkanolammonium ion, etc.).

$R_1$ represents a hydrogen atom, or a linear or branched alkyl group containing 5 to 40, preferably 12 to 36, and more preferably 16 to 22 carbon atoms.

The ingredient (a) is formed by copolymerization of a constitutional unit consisting of 2-acrylamide-2 methylpropanesulfonic acid or a salt thereof with a constitutional unit consisting of polyoxyethylene alkyl ether methacrylate. Such a copolymer may be or may not be crosslinked. A method for producing the ingredient (a) is not particularly limited. It can be produced by an ordinary method. Specifically, the copolymer of the present invention can be produced according to the methods for producing a polymer or a crosspolymer disclosed in the aforementioned prior-art publications such as Japanese patent publication of unexamined application No. 2004-315525 (Patent Literature 3) and Japanese patent publication of unexamined application No. 2005-336095 (Patent Literature 4). However, the production methods are not limited thereto.

Examples of the ingredient (a) include an Ammonium acryloyldimethyltaurate/Beheneth-25 Methacrylate Crosspolymer and an Ammonium Acryloyldimethyltaurate/Steareth-25 Methacrylate Crosspolymer (INCI name). The Ammonium acryloyldimethyltaurate/Beheneth-25 Methacrylate Crosspolymer is commercially available with a trade name of "Aristoflex HMB" (manufactured by Clariant). The Ammonium Acryloyldimethyltaurate/Steareth-25 Methacrylate Crosspolymer is commercially available with a trade name of "Aristoflex HMS" (manufactured by Clariant). These products can be preferably used. One or more types of the ingredient (a) can be used.

The ingredient (a) is mixed into the skin cosmetic preparation of the present invention at a mass percentage of preferably 0.005% to 2.0% by mass, more preferably 0.01% to 1.5% by mass, and particularly preferably 0.01% to 1.0% by mass. If the mass percentage of the ingredient (a) mixed is less than 0.005% by mass, it becomes difficult for the cosmetic preparation to sufficiently permeate to skin. On the other hand, if the ingredient (a) is mixed at a mass percentage of more than 2.0% by mass, the viscosity of the cosmetic preparation as a whole is increased, and thus the cosmetic preparation is likely to lose its dewy, watery feeling and its permeation to skin.

An alkyl modified carboxyvinyl polymer used as ingredient (b) in the skin cosmetic preparation of the present invention has been known as an INCI name of Acrylates/C10-30 Alkyl Acrylate Crosspolymer or the like. Thus, a commercially available product can be used as such an alkyl modified carboxyvinyl polymer. Specific examples of such a commercially available product include: Acritamer 501ED and Acritamer505ED (both of which are manufactured by Rita Corporation); Aqupec HV-501ER (manufactured by Sumitomo Seika Chemical Co., Ltd.); Carbopol ETD 2020 Polymer, Carbopol 1342 Polymer, Carbopol 1382 Polymer, Carbopol Ultrez 20 Polymer, Carbopol Ultrez 21 Polymer, Pemulen TR-1, and Pemulen TR-2 (all of which are manufactured by Noveon); and Tego Carbomer 341ER (manufactured by Degussa Care & Surface Specialties). These products can be preferably used. One or more types of the ingredient (b) can be used.

The ingredient (b) is mixed into the skin cosmetic preparation of the present invention at a mass percentage of preferably 0.005% to 1.5% by mass, more preferably 0.01% to 1.0% by mass, and particularly preferably 0.01% to 0.3% by mass. If the mass percentage of the ingredient (b) mixed is less than 0.005% by mass, it becomes difficult to keep the emulsion stability of oil ingredient. On the other hand, if the ingredient (b) is mixed at a mass percentage of more than 1.5% by mass, it becomes poor to permeate to skin, and an unfavorable slippy feeling is generated. Further, unfavorably, stickiness also tends to appear.

The ingredient (c) in the skin cosmetic preparation of the present invention is an alkylene oxide derivative represented by the following formula (II):

$$R_2O\text{-}[(AO)_a(EO)_b]\text{---}R_3 \quad (II)$$

In the above formula (II), AO represents an oxyalkylene group containing 3 or 4 carbon atoms. Specific examples of AO include an oxypropylene group, an oxybutylene group, an oxyisobutylene group, an oxytrimethylene group, and an oxytetramethylene group. An oxypropylene group and an oxybutylene group are preferable. EO represents an oxyethylene group.

The symbol a represents an average number of moles added of AO, and it is $1 \leq a \leq 70$, and preferably $2 \leq a \leq 20$. The symbol b represents an average number of moles added of EO, and it is $1 \leq b \leq 70$, and preferably $2 \leq b \leq 20$. If such a and b are less than 1, a moisturizing effect is decreased. In contrast, if such a and b exceed 70, stickiness appears and a sufficient smoothing effect cannot be obtained. It is to be noted that (a+b) is preferably 8 to 100. If the (a+b) value is too large, stickiness may appear.

The mass percentage of EO to the sum of AO and EO [EO/(AO+EO)] is preferably 20% to 80% by mass. If the mass percentage of EO is less than 20% by mass, it tends to be poor in terms of a moisturizing effect. On the other hand, if it exceeds 80% by mass, it tends to be poor in terms of a smoothing effect.

The order of adding AO and EO is not particularly limited. In addition, AO and EO may be added in a block state or in a random state. Such block states include not only 2-stage block but also 3- or more stage block. A random state addition is preferable.

Each of $R_2$ and $R_3$ independently represents an alkyl group containing 1 to 4 carbon atoms. Specific examples of such an alkyl group include a methyl group, an ethyl group, an n-propyl group, an isopropyl group, an n-butyl group, a sec-butyl group, and a tert-butyl group. A methyl group and an ethyl group are preferable. If an alkyl group containing 5 or more carbon atoms is used, hydrophilicity is decreased, and a moisturizing effect is decreased.

The ingredient (c) can be produced by a known method. For example, ethylene oxide and alkylene oxide containing 3 or 4 carbon atoms are added to a compound having a hydroxyl group for polymerization. Thereafter, a halogenated alkyl is allowed to react with an ether in the presence of an alkaline catalyst. However, examples of such a production method are not limited thereto. One or more types of the ingredient (c) can be used.

The ingredient (c) is mixed into the skin cosmetic preparation of the present invention at a mass percentage of preferably 0.005% to 15.0% by mass, more preferably 0.01% to 12.0% by mass, and particularly preferably 0.5% to 12.0% by mass. If the mass percentage of the ingredient (c) mixed is less than 0.005% by mass, there may be cases where the effect of the ingredient (c) cannot be sufficiently obtained. On the other hand, if the ingredient (c) is mixed at a mass percentage of more than 15.0% by mass, stickiness may be felt after the use of the present cosmetic preparation.

The skin cosmetic preparation of the present invention may further comprise, as ingredient (d), oil that has a viscosity at 25° C. of 100 mPa·s or less and is a liquid at an ordinary temperature, as well as the aforementioned essentially-mixed ingredients (a) to (c), so as to improve effects as an skin milk, such as a moisturizing effect and a softening effect on skin.

The type of such an ingredient (d) is not particularly limited, as long as it is generally used as a cosmetic ingredient. Examples of such an ingredient (d) that can be used, as appropriate, include hydrocarbon oil, branched fatty acid, branched unsaturated alcohol, ester oil, ether oil, and silicone oil.

Specific examples of hydrocarbon oil include squalane (a viscosity at 25° C. of 32 mPa·s; hereafter only such a viscosity value at 25° C. is described), squalene (35 mPa·s), liquid paraffin (43 mPa·s), an α-olefin oligomer (45 mPa·s), hydrogenated polyisobutene (70 mPa·s), and isoparaffin (30 mPa·s).

In addition, examples of branched fatty acid and branched unsaturated alcohol include isostearic acid (77 mPa·s), isostearyl alcohol (56 mPa·s), octyldodecanol (57 mPa·s), hexyldodecanol (41 mPa·s), decyltetradecanoyl (81 mPa·s), and oleyl alcohol (33 mPa·s).

Moreover, examples of ester oil include 2-ethylhexyl 2-ethylhexanoate (11 mPa·s), isononyl 2-ethylhexanoate (12 mPa·s), diisobutyl adipate (6 mPa·s), di-2-ethylhexyl succinate (11 mPa·s), cetyl 2-ethylhexanoate (13 mPa·s), 2-hexyldecyl 2-ethylhexanoate (11 mPa·s), neopentyl glycol di-2-ethylhexanoate (13 mPa·s), trimethylolpropane tri-2-ethylhexanoate (52 mPa·s), tri(capryl/capric acid) glycerin (25 mPa·s), neopentyl glycol dicaprate (19 mPa·s), 2-ethylhexyl isononanoate (5 mPa·s), isononyl isononanoate (6 mPa·s), isodecyl isononanoate (7 mPa·s), isotridecyl isononanoate (12 mPa·s), hexyl laurate (6 mPa·s), isopropyl myristate (5 mPa·s), 2-hexyldecyl myristate (5 mPa·s), 2-octyldodecyl myristate (28 mPa·s), isopropyl palmitate (7 mPa·s), 2-ethylhexyl palmitate (11 mPa·s), 2-hexyldecyl stearate (27 mPa·s), ethyl isostearate (8 mPa·s), isopropyl isostearate (10 mPa·s), 2-hexyldecyl isostearate (34 mPa·s), isostearyl isostearate (38 mPa·s), isodecyl neopentanoate (4 mPa·s), isostearyl neopentanoate (16 mPa·s), octyldodecyl neopentanoate (15 mPa·s), 2-octyldodecyl dimethyloctanoate (25 mPa·s), 2-ethylhexyl hydroxystearate (64 mPa·s), 2-octyldodecyl 12-stearoylstearate (89 mPa·s), oleyl oleate (28 mPa·s), 2-ethylhexyl salicylate (9 mPa·s), and dialkyl carbonate (55 mPa·s).

Examples of ether oil include dioctyl ether and polyoxyethylene/polyoxypropylene dimethyl ether.

Examples of silicone oil include octamethyl trisiloxane (1 mPa·s), decamethyl tetrasiloxane (1.5 mPa·s), decamethyl cyclopentasiloxane (4 mPa·s), caprylmethicone (10 mPa·s), and methyl polysiloxane.

When the ingredient (d) is mixed into the skin cosmetic preparation of the present invention, it is mixed at a mass percentage of preferably 1.0% to 10.0% by mass, and more preferably 5.0% to 10.0% by mass. If the mixed amount is less than 1.0% by mass, the improvement of effects as an skin milk, such as a moisturizing effect and a softening effect on skin, cannot be sufficiently satisfactory. On the other hand, if the mixed amount exceeds 10.0% by mass, there is a fear that it causes a problem regarding stability as an emulsified cosmetic preparation. One or more types of the ingredient (d) can be used.

The oil-in-water emulsified skin cosmetic preparation of the present invention has a viscosity at 25° C. of 10,000 mPa·s or less, preferably 9,500 mPa·s or less, and particularly preferably 8,000 mPa·s or less. When the viscosity exceeds 10,000 mPa·s, the cosmetic preparation loses water texture and dewy feeling as a lotion, and it is not preferable. In the present invention, even a cosmetic preparation having a viscosity that is less than the aforementioned preferred viscosity, and further, having a relatively low viscosity, can be provided as a highly stable oil-in-water emulsified milky skin cosmetic preparation without creaming. This is particularly because of a synergistic effect between the function as an emulsifier and the function of a thickener caused by the ingredient (a) and the ingredient (b) comprised in the cosmetic preparation of the present invention. Accordingly, the lower limit of the viscosity of the present invention is not particularly limited. However, approximately 2,000 mPa·s or more is rather preferable.

The viscosity (25° C.) of the skin cosmetic preparation of the present invention is measured using a Vismetron viscometer. Specifically, a digital Vismetron viscometer VDA2 (manufactured by Shibaura System Co., Ltd.) is used, for example. A test sample contained in a measurement vessel is immersed in a 25° C. thermobath for 1 hour, and the viscosity thereof is then measured with rotor No. 4 at a rotation number of 30 rpm.

The oil-in-water emulsified skin cosmetic preparation of the present invention shows an excellent stability with milky white color although it contains relatively large amount of water and has a low viscosity. Thus, it leads the skin cosmetic preparation to impart a water texture and dewy feeling as a skin lotion with milky creaminess which is generally achieved by a skin milk. Water is added into the oil-in-water emulsified skin cosmetic preparation at a mass percentage of preferably 55% to 80% by mass. If the added amount of water is less than 55% by mass, the skin cosmetic preparation may lack a water texture and dewy feeling as a skin lotion. On the other hand, if the added amount of water exceeds 80% by mass, an emollient feeling required as skin milk may not be achieved sufficiently.

The oil-in-water emulsified skin cosmetic preparation of the present invention can be produced by an ordinary method. For example, while the ingredients of a aqueous phase are mixed and stirred with a homomixer, an oil ingredient is gradually added thereto and is then emulsified, so as to produce the aforementioned cosmetic preparation. However, the production method is not limited to the method described herein.

The oil-in-water emulsified skin cosmetic preparation of the present invention is clouded, presenting a milky white color. Such white turbidity of the cosmetic preparation of the present invention can be determined based on the measurement results of the L value (transparency; as the L value is close to 100, such transparency is increased) of the skin cosmetic preparation obtained using a spectrophotometer. The measurement of the L value is generally used to measure a color difference. The L value correlates with white turbidity, and thus the value can be used as an index of the degree of white turbidity. In the case of the skin cosmetic preparation of the present invention, the L value is preferably approximately 45 or less, more preferably approximately 40 or less, and particularly preferably approximately 35 or less.

The oil-in-water emulsified milky skin cosmetic preparation of the present invention may also comprise, as necessary, any other additive ingredients that are generally used in external skin preparations such as cosmetic preparations or pharmaceuticals, within a range that does not impair the effects of the present invention. Examples of such other additive ingredients include powder ingredients, solid oil and fat, wax, hydrocarbon, higher fatty acid, higher alcohol, an ester, silicone, an anionic surfactant, a cationic surfactant, an amphoteric surfactant, a nonionic surfactant, a water-soluble polymer, a thickener, a coating agent, an ultraviolet absorber, a sequestering agent, lower alcohol, polyhydric alcohol, sugar, amino acid, organic amine, polymer emulsion, a pH adjuster, a skin nutrient agent, vitamin, an antioxidant, an antioxidizing auxiliary agent, aromatic, and water.

Examples of powder ingredients include: inorganic powders (e.g. talc, kaoline, mica, sericite, muscovite, phlogopite, synthetic mica, lepidolite, black mica, vermiculite, magnesium carbonate, calcium carbonate, aluminum silicate, barium silicate, calcium silicate, magnesium silicate, strontium silicate, metal tungstate, magnesium, silica, zeolite, barium sulfate, calcined calcium sulfate (calcined gypsum), calcium phosphate, fluorine apatite, hydroxyapatite, ceramic powders, metallic soap (e.g. zinc myristate, calcium palmitate, and aluminum stearate), boron nitride, etc.); organic powders (e.g. polyamide resin powders (nylon powders), polyethylene powders, methyl polymethacrylate powders, polystyrene powders, copolymer resin powders of styrene and acrylic acid, benzoguanamine resin powders, polytetrafluoride ethylene powders, cellulose powders, etc.); inorganic white pigments (e.g. titanium dioxide, zinc oxide, etc.); inorganic red pigments (e.g. iron oxide (colcothar), iron titanate, etc.); inorganic brown pigments (e.g. g-iron oxide, etc.); inorganic yellow pigments (e.g. yellow iron oxide, loess, etc.); inorganic black pigments (e.g. black iron oxide, lower titanium oxide, etc.); inorganic violet pigments (e.g. mango violet, cobalt violet, etc.); inorganic green pigments (e.g. chromium oxide, chromium hydroxide, cobalt titanate, etc.); inorganic blue pigments (e.g. ultramarine blue, iron blue, etc.); pearl pigments (e.g. titanium oxide-coated mica, titanium oxide-coated bismuth oxychloride, titanium oxide-coated talc, colored titanium oxide-coated mice, bismuth oxychloride, argentine, etc.); metal powder pigments (e.g. aluminum powders, copper powders, etc.); organic pigments such as zirconium, barium or aluminum lake (e.g. organic pigments such as red No. 201, red No. 202, red No. 204, red No. 205, red No. 220, red No. 226, red No. 228, red No. 405, orange No. 203, orange No. 204, yellow No. 205, yellow No. 401 and blue No. 404, red No. 3, red No. 104, red No. 106, red No. 227, red No. 230, red No. 401, red No. 505, orange No. 205, yellow No. 4, yellow No. 5, yellow No. 202, yellow No. 203, green No. 3, and blue No. 1); and natural pigments (e.g. chlorophyll, b-carotene, etc.).

Examples of solid oil and fat include cacao butter, coconut oil, horse fat, hydrogenated coconut oil, palm oil, tallow, mutton tallow, hydrogenated tallow, palm kernel oil, lard, beef bone fat, Japan tallow kernel oil, hydrogenated oil, hoof oil, Japan tallow, and hydrogenated castor oil.

Examples of wax include bee wax, candelilla wax, cotton wax, carnauba wax, bayberry wax, Chinese wax, spermaceti, montan wax, rice bran wax, lanolin, kapok wax, lanolin acetate, liquid lanolin, sugarcane wax, lanolin fatty acid isopropyl, hexyl laurate, reduced lanolin, *Simmondsia chinensis* wax, hard lanolin, shellac wax, POE lanolin alcohol ether, POE lanolin alcohol acetate, POE cholesterol ether, lanolin fatty acid polyethylene glycol, and POE hydrogenated lanolin alcohol ether.

Examples of higher fatty acid include lauric acid, myristic acid, palmitic acid, stearic acid, behenic acid, oleic acid, undecylenic acid, tall acid, isostearic acid, linolic acid, linolenic acid, eicosapentaenoic acid (EPA), and docosahexaenoic acid (DHA).

Examples of higher alcohol include: linear alcohol (e.g. lauryl alcohol, cetyl alcohol, stearyl alcohol, behenyl alcohol, myristyl alcohol, oleyl alcohol, cetostearyl alcohol, etc.); and branched-chain alcohol (e.g. monostearyl glycerin ether (batyl alcohol), 2-decyltetradecinol, lanolin alcohol, cholesterol, phytosterol, hexyl dodecanol, isostearyl alcohol, octyl dodecanol, etc.).

Examples of an anionic surfactant include: fatty acid soap (e.g. sodium laurate, sodium palmitate, etc.); higher alkyl sulfate (e.g. sodium lauryl sulfate, potassium lauryl sulfate, etc.); alkyl ether sulfate (e.g. POE-triethanolamine lauryl sulfate, POE-sodium lauryl sulfate, etc.); N-acylsarcosinic acid (e.g. sodium lauroyl sarcosine, etc.); higher fatty acid amide sulfonate (e.g. sodium N-myristoyl-N-methyltaurine, sodium coconut oil fatty acid methyl taurid, sodium lauryl methyl taurid, etc.); phosphate (e.g. POE-sodium oleyl ether phosphate, POE-stearyl ether phosphate, etc.); sulfosuccinate (e.g. sodium di-2-ethylhexylsulfosuccinate, sodium monolauroyl monoethanol amide polyoxyethylene sulfosuccinate, sodium lauryl polypropylene glycol sulfosuccinate, etc.); alkylbenzene sulfonate (e.g. sodium linear dodecylbenzene sulfonate, triethanolamine linear dodecylbenzene sulfonate, linear dodecylbenzene sulfonate, etc.); higher fatty acid ester sulfate (e.g. sodium hardened coconut oil fatty acid glycerin sulfate, etc.); N-acylglutamate (e.g. monosodium N-lauroylglutamate, disodium N-stearoylglutamate, monosodium N-myristoyl-L-glutamate, etc.); sulfonated oil (e.g. turkey red oil, etc.); POE-alkyl ether carboxylic acid; POE-alkylallyl ether carboxylate; a-olefinsulfonate; higher fatty acid ester sulfonate; secondary alcohol sulfate; higher fatty acid alkylolamide sulfate; sodium lauroyl monoethanol amide succinate; ditriethanolamine N-palmitoyl aspartate; and casein sodium.

Examples of a cationic surfactant include alkyl trimethyl ammonium salts (e.g. stearyl trimethyl ammonium chloride, lauryl trimethyl ammonium chloride, etc.); alkyl pyridinium ammonium salts (e.g. cetylpyridinium chloride, etc.); distearyl dimethyl ammonium dialkyl dimethyl ammonium chloride salts; poly(N,N'-dimethyl-3,5-methylene pyridinium chloride); alkyl quaternary ammonium salts; alkyl dimethyl benzyl ammonium salts; alkyl isoquinolinium salts; dialkyl morphonium salts; POE-alkylamine; alkylamine salts; polyamine fatty acid derivatives; amylalcohol fatty acid derivatives; benzalkonium chloride; and benzethonium chloride.

Examples of an amphoteric surfactant include: imidazoline amphoteric surfactants (e.g. sodium 2-undecyl-N,N,N-(hydroxyethylcarboxymethyl)-2-imidazoline, 2-cocoyl-2-imidazolinium hydroxide-1-carboxyethyloxy-2-sodium salt, etc.); and betaine surfactants (e.g. 2-heptadecyl-N-carboxymethyl-N-hydroxyethylimidazolinium betaine, lauryldimethylaminoacetic acid betaine, alkylbetaine, amidebetaine, sulfobetaine, etc.).

Examples of a lipophilic nonionic surfactant include: sorbitan fatty acid esters (e.g. sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, diglycerol sorbitan tetra-2-ethylhexylate, etc.); glycerin polyglycerin fatty acids (e.g. monocottonseed oil fatty acid glycerin, monoerucic acid glycerin, sesquioleic acid glycerin, monostearic acid glycerin, a,a'-oleic acid pyroglutamic acid glycerin, monostearic acid glycerin malic acid, etc.); propylene glycol fatty acid esters (e.g. propylene glycol monostearate, etc.); hardened castor oil derivatives; and glycerin alkyl ether.

Examples of a hydrophilic nonionic surfactant include: POE-sorbitan fatty acid esters (e.g. POE-sorbitan monooleate, POE-sorbitan monostearate, POE-sorbitan monooleate, POE-sorbitan tetraoleate, etc.); POE-sorbit fatty acid esters (e.g. POE-sorbit monolaurate, POE-sorbit monooleate, POE-sorbit pentaoleate, POE-sorbit monostearate, etc.); POE-glycerin fatty acid esters (e.g. POE-monooleates such as POE-glycerin monostearate, POE-glycerin monoisostearate, or POE-glycerin triisostearate); POE-fatty acid esters (e.g. POE-distearate, POE-monodioleate, ethylene glycol distearate, etc.); POE-alkyl ethers (e.g. POE-lauryl ether, POE-oleyl ether, POE-stearyl ether, POE-behenyl ether, POE-2-octyl dodecyl ether, POE-cholestanol ether, etc.); Pluronic-type products (e.g. Pluronic, etc.); POE•POP-alkyl ethers (e.g. POE•POP-cetyl ether, POE•POP-2-decyltetradecyl ether, POE•POP-monobutyl ether, POE•POP-hydrogenated lanolin, POE•POP-glycerin ether, etc.); tetra POE•tetra POP-ethylenediamine condensates (e.g. Tetronic, etc.); POE-castor oil hardened castor oil derivatives (e.g. POE-castor oil, POE-hardened castor oil, POE-hardened castor oil monoisostearate, POE-hardened castor oil triisostearate, POE-hardened castor oil monopyroglutamic acid monoisostearic acid diester, POE-hardened castor oil maleic acid, etc.); POE-beeswax•lanolin derivatives (e.g. POE-sorbit beeswax, etc.); alkanolamide (e.g. coconut oil fatty acid diethanolamide, lauric acid monoethanolamide, fatty acid isopropanolamide, etc.); POE-propylene glycol fatty acid ester; POE-alkylamine; POE-fatty acid amide; sucrose fatty acid ester; alkylethoxydimethylamine oxide; and trioleyl phosphate.

Examples of a natural water-soluble polymer include plant polymers (e.g. gum Arabic, gum tragacanth, galactan, Guar gum, Carob gum, karaya gum, carrageenan, pectin, agar, quince seed (*Cydonia oblonga*), algae colloid (brown algae extract), starch (rice, corn, potato, wheat), glycyrrhizinic acid); microorganism polymers (e.g. xanthan gum, dextran, succinoglucan, Pullulan, etc.); and animal polymers (e.g. collagen, casein, albumin, gelatin, etc.).

Examples of a semisynthetic water-soluble polymer include: starch polymers (e.g. carboxymethyl starch, methylhydroxypropyl starch, etc.); cellulose polymers (methyl cellulose, ethyl cellulose, methylhydroxypropyl cellulose, hydroxyethyl cellulose, cellulose sodium sulfate, hydroxypropyl cellulose, carboxymethyl cellulose, sodium carboxymethyl cellulose, crystalline cellulose, cellulose powders, etc.); and alginic acid polymers (e.g. sodium alginate, alginic acid propylene glycol ester, etc.).

Examples of a synthetic water-soluble polymer include: vinyl polymers (e.g. polyvinyl alcohol, polyvinyl methyl ether, polyvinylpyrrolidone, a carboxyvinyl polymer, etc.); polyoxyethylene polymers (e.g. polyoxyethylene-polyoxypropylene copolymers such as polyethylene glycol 20,000, 40,000 and 60,000, etc.); acrylic polymers (e.g. sodium polyacrylate, polyethyl acrylate, polyacrylamide, etc.); polyethyleneimine; and a cation polymer.

Examples of a thickener include gum Arabic, carrageenan, karaya gum, gum tragacanth, Carob gum, quince seed (*Cydonia oblonga*), casein, dextrin, gelatin, sodium pectate, sodium alaginate, methyl cellulose, ethyl cellulose, CMC, hydroxyethyl cellulose, hydroxypropyl cellulose, PVA, PVM, PVP, sodium polyacrylate, a carboxyvinyl polymer, Locust bean gum, Guar gum, tamarind gum, dialkyldimethylammonium sulfate cellulose, xanthan gum, magnesium aluminum silicate, bentonite, hectorite, AlMg silicate (bee gum), laponite, and silicic acid anhydride.

Examples of an ultraviolet absorber include benzoate ultraviolet absorbers (e.g. paraaminobenzoic acid (hereinafter abbreviated as PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, N,N-dimethyl PABA ethyl ester, etc.); anthranilic acid ultraviolet absorbers (e.g. homomenthyl-N-acetylanthranilate, etc.); salicylic acid ultraviolet absorbers (e.g. amyl salicylate, menthyl salicylate, homomenthyl salicylate, octyl salilcylate, phenyl salicylate, benzyl salicylate, p-isopropanolphenyl salicylate, etc.); cinnamic acid ultraviolet absorbers (e.g. octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxy cinnamate, ethyl-a-cyano-b-phenyl cinnamate, 2-ethylhexyl-a-cyano-b-phenyl cinnamate, glycerylmono-2-ethylhexanoyl-diparamethoxy cinnamate, etc.); benzophenone ultraviolet absorbers (e.g. 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, 4-hydroxy-3-carboxybenzophenone, etc.); 3-(4'-methylbenzylidene)-d,l-camphor, 3-benzylidene-d,l-camphor; 2-phenyl-5-methylbenzoxazole; 2,2'-hydroxy-5-methylphenylbenzotriazole; 2-(2'-hydroxy-5'-t-octylphenyl)benzotriazole; 2-(2'-hydroxy-5'-methylphenylbenzotriazole; dibenzalazine; dianisoylmethane; 4-methoxy-4'-t-butyldibenzoylmethane; and 5-(3,3-dimethyl-2-norbornylidene) 3-pentane-2-one.

Examples of a sequestering agent include 1-hydroxyethane-1,1-diphosphonic acid, a tetrasodium salt of 1-hydroxyethane-1,1-diphosphonic acid, disodium edetate, trisodium edetate, tetrasodium edetate, sodium citrate, sodium polyphosphate, sodium methaphosphate, gluconic acid, phosphoric acid, citric acid, ascorbic acid, succinic acid, edetic acid, and trisodium ethylenediaminehydroxyethyl triacetate.

Examples of lower alcohol include ethanol, propanol, isopropanol, isobutyl alcohol, and t-butyl alcohol.

Examples of polyhydric alcohol include: dihydric alcohol (e.g. ethylene glycol, propylene glycol, trimethylene glycol, 1,2-butylene glycol, 1,3-butylene glycol, tetramethylene glycol, 2,3-butylene glycol, pentamethylene glycol, 2-butene-1, 4-diol, hexylene glycol, octylene glycol, etc.); trihydric alcohol (e.g. glycerin, trimethylolpropane, etc.); tetrahydric alcohol (e.g. pentaerythritol such as 1,2,6-hexanetriol, etc.); pentahydric alcohol (e.g. xylitol, etc.); hexahydric alcohol (e.g. sorbitol, mannitol, etc.); polyhydric alcohol polymers (e.g. diethylene glycol, dipropylene glycol, triethylene glycol, polypropylene glycol, tetraethylene glycol, diglycerin, polyethylene glycol, triglycerin, tetraglycerin, polyglycerin, etc.); divalent alcohol alkyl ethers (e.g. ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether, etc.); dihydric alcohol alkyl ethers (e.g. diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether, etc.); dihydric alcohol ether esters (e.g. ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate, etc.); glycerin monoalkyl ethers (e.g. xyl alcohol, selachyl alcohol, batyl alcohol, etc.); sugar alcohol (e.g. sorbitol, maltitol, maltotriose, mannitol, sucrose, erythritol, glucose, fructose, amylolytic sugar, maltose, xylitose, amylolytic sugar reduced alcohol, etc.); glysolid; tetrahydrofurfuryl alcohol; POE-tetrahydrofurfuryl alcohol; POP-butyl ether; POP•POE-butyl ether; tripolyoxypropylene glycerin ether; POP-glycerin ether; POP-glycerin ether phosphoric acid; POP•POE-pentaerythritol ether; and polyglycerin.

Examples of monosaccharide include: triose (e.g. D-glycerylaldehyde, dihydroxyacetone, etc.); tetrose (e.g. D-erythrose, D-erythrulose, D-threose, erythritol, etc.); pentose (e.g. L-arabinose, D-xylose, L-lyxose, D-arabinose, D-ribose, D-ribulose, D-xylulose, L-xylulose, etc.); hexose (e.g. D-glucose, D-talose, D-psicose, D-galactose, D-fructose, L-galactose, L-mannose, D-tagatose, etc.); heptose (e.g. aldoheptose, heplose, etc.); octose (e.g. octulose, etc.); deoxy sugar (e.g. 2-deoxy-D-ribose, 6-deoxy-L-galactose, 6-deoxy-L-mannose, etc.); amino sugar (e.g. D-glucosamine, D-galactosamine, sialic acid, aminouronic acid, muramic acid, etc.); and uronic acid (e.g. D-glucuronic acid, D-mannuronic acid, L-guluronic acid, D-galacturonic acid, L-iduronic acid, etc.).

Examples of oligosaccharide include sucrose, gunchianose, umbelliferose, lactose, planteose, isolichnoses, a,a-trehalose, raffinose, lichnoses, umbilicine, and stachyose verbascoses.

Examples of polysaccharides include cellulose, quince seed, chondroitin sulfuric acid, starch, galactan, dermatan sulfuric acid, glycogen, gum Arabic, heparin sulfuric acid, hyaluronic acid, gum tragacanth, keratan sulfuric acid, chondroitin, xanthan gum, mucoitinsulfuric acid, Guar gum, dextran, keratosulfuric acid, locust bean gum, succinoglucan, and charonin acid.

Examples of amino acid include neutral amino acids (e.g. threonine, cysteine, etc.); and basic amino acids (e.g. hydroxylysine, etc.). Further, examples of amino acid derivatives include sodium acylsarcosine (sodium lauroylsarcosine), acyl glutamate, acyl-b-alanine sodium, glutathione, and pyrrolidone carboxylic acid.

Examples of organic amine include monoethanolamine, diethanolamine, triethanolamine, morpholine, triisopropanolamine, 2-amino-2-methyl-1,3-propanediol, and 2-amino-2-methyl-1-propanol.

Examples of polymer emulsion include acrylic resin emulsion, polyacrylic acid ethyl emulsion, acrylic resin solution, polyacryl alkyl ester emulsion, polyvinyl acetate resin emulsion, and natural rubber latex.

Examples of a pH adjuster include buffers such as lactic acid-sodium lactate, citric acid-sodium citrate, and succinic acid-sodium succinate.

Examples of vitamin include: vitamin A, vitamin B1, vitamin B2, vitamin B6, vitamin C, vitamin E, and the derivatives thereof; pantothenic acid and the derivative thereof; and biotin.

Examples of an antioxidant include tocopherols, dibutyl hydroxytoluene, butylhydroxyanisol, and gallic acid esters.

Examples of an antioxidizing auxiliary agent include phosphoric acid, citric acid, ascorbic acid, maleic acid, malonic acid, succinic acid, fumaric acid, cephalin, hexametaphosphate, phytic acid, and ethylenediamine tetraacetic acid.

Examples of other ingredients that can be mixed into the cosmetic preparation include: antiseptic agents (e.g. ethylparaben, butylparaben, etc.); antiphlogistic agents (e.g. a glycyrrhizinic acid derivative, a glycyrrhetinic acid derivative, a salicylic acid derivative, hinokitiol, zinc oxide, allantoin, etc.); skin whitening agents (e.g. placental extracts, saxifragaceous extracts, arbutin, etc.); various types of extracts (e.g. cork tree bark, coptis root, lithospermi radix, peony root, swertia herb, birch, sage, loquat, carrots, aloe, tree mallow, iris, grapes, coix seed, loofah, lily, saffron, Cnidium Rhizome, ginger, hypericum, ononis, garlic, capsicum, citrus unshiu peel, Japanese angelica root, seaweed, etc.); activator agents (e.g. royal jelly, a photosensitive pigment, a cholesterol derivative, etc.); blood circulation promoters (e.g. nonylic acid vanillylamide, nicotinic acid benzyl ester, nicotinic acid b-butoxy ethyl ester, capsaicin, gingerone, cantharides tincture, ichthammol, tannic acid, a-borneol, nicotinic acid tocopherol, inositol hexanicotinate, cyclandelate, cinnarizine, tolazoline, acetylcholine, verapamil, cepharanthine, g-orizanol, etc.); antiseborrheic agents (e.g. sulfur, thianthol, etc.); and anti-inflammatory agents (e.g. tranexamic acid, thiotaurine, hypotaurine, etc.).

EXAMPLES

The present invention will be described more in detail based on the following examples. However, these examples are not intended to limit the scope of the present invention. It is to be noted that all the mixed amounts are expressed with % by mass.

First, test methods for each evaluation and evaluation criteria used in the present examples will be described below.

<Viscosity (Initial Viscosity)>

Using a digital Vismetron viscometer VDA2 (manufactured by Shibaura System Co., Ltd.), a test sample placed in a measurement vessel was immersed in a 25° C. thermobath for 1 hour, and it was then measured with rotor No. 4 at a rotation number of 30 rpm.

<Degree of White Turbidity>

The degree of white turbidity of a test sample was measured by measuring an L value (transparency; as the L value is close to 100, such transparency is increased) using an integrating-sphere photometer ("Color-Eye 7000A"; manufactured by GretagMacbeth).

<Stability>

A test sample was left for 1 month at each temperatures of 0° C., 25° C. and 50° C. Thereafter, the appearance of the test sample was observed with naked eyes and under a microscope, and a determination was then made according to the following evaluation criteria.

(Evaluation Criteria)

A: Separation and precipitation of crystals were not observed at all.

B: Almost no separation and precipitation of crystals were observed.

C: Separation of the liquid phase (oil phase or aqueous phase) or crystal precipitation, and a significant decrease in the viscosity (a decrease in a viscosity of 1,000 mPa·s or more from the initial viscosity) were observed.

<Feeling of Use; Dewy, Watery Feeling when Applied>

An actual use test was carried out with professional female panelists (10 people). The panelists evaluated dewy, watery feeling felt when the skin cosmetic preparation of the present invention was applied, according to the following evaluation criteria.

(Evaluation Criteria)

A: All the 10 panelists evaluated that the skin cosmetic preparation had dewy, watery feeling.

B: 7 to 9 out of the 10 panelists evaluated that the skin cosmetic preparation had dewy, watery feeling.

C: 3 to 6 out of the 10 panelists evaluated that the skin cosmetic preparation had dewy, watery feeling.

D: 0 to 2 out of the 10 panelists evaluated that the skin cosmetic preparation had dewy, watery feeling.

<Feeling of Use: No Stickiness>

An actual use test was carried out with professional female panelists (10 people). The panelists evaluated stickiness felt when the skin cosmetic preparation of the present invention was applied, according to the following evaluation criteria.

(Evaluation Criteria)

A: All the 10 panelists evaluated that the skin cosmetic preparation had no stickiness and kept moist.

B: 7 to 9 out of the 10 panelists evaluated that the skin cosmetic preparation had no stickiness and kept moist.

C: 3 to 6 out of the 10 panelists evaluated that the skin cosmetic preparation had no stickiness and kept moist.

D: 0 to 2 out of the 10 panelists evaluated that the skin cosmetic preparation had no stickiness and kept moist.

<Feeling of Use: Refreshing Feeling>

An actual use test was carried out with professional female panelists (10 people). The panelists evaluated refreshing feeling felt when the skin cosmetic preparation of the present invention was applied, according to the following evaluation criteria.

(Evaluation Criteria)
A: All the 10 panelists evaluated that the skin cosmetic preparation had refreshing feeling.
B: 7 to 9 out of the 10 panelists evaluated that the skin cosmetic preparation had refreshing feeling.
C: 3 to 6 out of the 10 panelists evaluated that the skin cosmetic preparation had refreshing feeling.
D: 0 to 2 out of the 10 panelists evaluated that the skin cosmetic preparation had refreshing feeling.

<Feeling of Use: Emollient Feeling (Feeling of Use for Giving Softness to Skin)>

An actual use test was carried out with professional female panelists (10 people). The panelists evaluated an emollient feeling obtained when the skin cosmetic preparation of the present invention was applied, according to the following evaluation criteria.
(Evaluation Criteria)
A: All the 10 panelists evaluated that the skin cosmetic preparation had an emollient feeling (feeling of use for giving softness to skin).
B: 7 to 9 out of the 10 panelists evaluated that the skin cosmetic preparation had an emollient feeling (feeling of use for giving softness to skin).
C: 3 to 6 out of the 10 panelists evaluated that the skin cosmetic preparation had an emollient feeling (feeling of use for giving softness to skin).
D: 0 to 2 out of the 10 panelists evaluated that the skin cosmetic preparation had an emollient feeling (feeling of use for giving softness to skin).

The ingredients (polymers and compounds) used in the present example are as follows.

Polymer (a1): a copolymer wherein, in the above formula (I), m/n=4 (m=80 mol %, n=20 mol %), p=10, $R_1$ is $C_{22}H_{45}$, and $X^+$ is $NH_4^+$ Polymer (a2): a copolymer wherein, in the above formula (I), m/n=9 (m=90 mol %, n=10 mol %), p=20, $R_1$ is $C_{18}H_{37}$, and $X^+$ is $NH_4^+$ Polymer (a3): a copolymer wherein, in the above formula (I), m/n=32.3 (m=97 mol %, n=3 mol %), p=25, $R_1$ is $C_{22}H_{45}$, and $X^+$ is $NH_4^+$ Polymer (a4): a copolymer wherein, in the above formula (I), m/n=49 (m=98 mol %, n=2 mol %), p=30, $R_1$ is $C_{22}H_{45}$, and $X^+$ is $NH_4^+$ Polymer (a5): a copolymer wherein, in the above formula (I), m/n=99 (m=99 mol %, n=1 mol %), p=45, $R_1$ is $C_{22}H_{45}$, and $X^+$ is $Na^+$ Polymer (a6): a copolymer wherein, in the above formula (I), m/n=49 (m=98 mol %, n=2 mol %), p=30, $R_1$ is $C_{22}H_{45}$, and $X^+$ is $Na^+$ Comparative polymer (a1): a copolymer wherein, in the above formula (I), m/n=1 (m=50 mol %, n=50 mol %), p=25, $R_1$ is $C_{22}H_{45}$, and $X^+$ is $Na^+$ Comparative polymer (a2): a copolymer wherein, in the above formula (I), m/n=1 (m=50 mol %, n=50 mol %), p=60, $R_1$ is $C_{22}H_{45}$, and $X^+$ is $NH_4^+$ Compound (b1): "Pemulen TR-2" (manufactured by Noveon) was used.

Compound (b2): "Aqupec HV-501ER" (manufactured by Sumitomo Seika Chemical Co., Ltd.) was used.

Comparative compound (b1): A carbomer ("Synthalen L" manufactured by 3V Group) was used.

Compound (c1): a compound wherein, in the above formula (II), $R_2$ is $CH_3$, AO is —$CH(CH_3)CH_2O$ (oxypropylene group), EO is $CH_2CH_2O$ (oxyethylene group), a=10, b=10, and $R_3$ is $CH_3$ (AO and EO are added randomly)

Compound (c2): a compound wherein, in the above formula (II), $R_2$ is $CH_3$, AO is —$CH(CH_3)CH_2O$ (oxypropylene group), EO is $CH_2CH_2O$ (oxyethylene group), a=5, b=15, and $R_3$ is $CH_3$ (AO and EO are added randomly)

Compound (c3): a compound wherein, in the above formula (II), $R_2$ is $CH_3$, AO is —$CH(CH_3CH_2)CH_2O$ (oxybutylene group), EO is $CH_2CH_2O$ (oxyethylene group), a=7, b=14, and $R_3$ is $CH_3$ (AO and EO are added randomly)

Comparative compound (c1): a compound wherein, in the above formula (II), $R_2$ is H, AO is —$CH(CH_3)CH_2O$ (oxypropylene group), EO is $CH_2CH_2O$ (oxyethylene group), a=10, b=10, and $R_3$ is H (AO and EO are added randomly)

Comparative compound (c2): a compound wherein, in the above formula (II), $R_2$ is $C_{12}H_{25}$, AO is —$CH(CH_3)CH_2O$ (oxypropylene group), EO is $CH_2CH_2O$ (oxyethylene group), a=10, b=10, and $R_3$ is $CH_3$ (AO and EO are added randomly)

Examples 1-5, Comparative Examples 1-5

Skin cosmetic preparations having the compositions as shown in Table 1 below were prepared by the following production method. These skin cosmetic preparations were evaluated by the aforementioned test method according to the aforementioned evaluation criteria in terms of feeling of use, viscosity and stability. The results are shown in Table 1.
(Production Method)
Ingredients (1) to (19), (23), (25) and (26) were uniformly dissolved at an ordinary temperature (phase A). Subsequently, ingredients (20) to (22), (24) and (27) were uniformly dissolved at an ordinary temperature (phase B). Thereafter, phase B was gradually added to the phase A that was being stirred with a homomixer at an ordinary temperature, and it was then emulsified, so as to obtain an oil-in-water emulsified milky skin cosmetic preparation of interest.

TABLE 1

| | Example | | | | | Comparative Example | | | | |
|---|---|---|---|---|---|---|---|---|---|---|
| | 1 | 2 | 3 | 4 | 5 | 1 | 2 | 3 | 4 | 5 |
| (1) Ion exchanged water | Balance | Balance | Balance | Balance | Balance | Balance | Balance | Balance | Balance | Balance |
| (2) Ethanol | 5.0 | 5.0 | 5.0 | 5.0 | 5.0 | 5.0 | 5.0 | 5.0 | 5.0 | 5.0 |
| (3) Glycerin | 4.0 | 10.0 | 3.0 | 7.0 | 5.0 | 4.0 | 10.0 | 3.0 | 7.0 | 5.0 |
| (4) 1,3-butylene glycol | 5.0 | 5.0 | 5.0 | 5.0 | 5.0 | 5.0 | 5.0 | 5.0 | 5.0 | 5.0 |
| (5) Polyethylene glycol 1500 | 3.0 | 3.0 | 3.0 | 3.0 | 3.0 | 3.0 | 3.0 | 3.0 | 3.0 | 3.0 |
| (6) Polyethylene glycol 2000 | 2.0 | 5.0 | 5.0 | 5.0 | 5.0 | 2.0 | 5.0 | 5.0 | 5.0 | 5.0 |
| (7) Polymer (a1) | 0.01 | 1.0 | 0.3 | 0.5 | 0.1 | — | 1.0 | 0.3 | — | 0.1 |
| (8) Polymer (a4) | — | 0.1 | — | 0.5 | 0.1 | — | — | — | — | 0.1 |
| (9) Polymer (a6) | — | — | 0.5 | — | 0.1 | — | — | 0.5 | — | 0.1 |
| (10) Comparative polymer (a1) | — | — | — | — | — | 0.01 | — | — | 0.5 | — |
| (11) Comparative polymer (a2) | — | — | — | — | — | — | 0.1 | — | 0.5 | — |
| (12) Compound (b2) | 0.2 | 1.0 | 0.03 | 0.01 | 0.5 | 0.2 | 0.05 | — | — | — |
| (13) Comparative compound (b1) | — | — | — | — | — | — | — | 0.03 | 0.01 | 0.07 |

TABLE 1-continued

| | Example | | | | | Comparative Example | | | | |
|---|---|---|---|---|---|---|---|---|---|---|
| | 1 | 2 | 3 | 4 | 5 | 1 | 2 | 3 | 4 | 5 |
| (14) Compound (c1) | 1.0 | — | 0.1 | — | 0.1 | 1.0 | — | 0.1 | — | — |
| (15) Compound (c2) | — | 0.01 | 10.0 | 5.0 | 0.1 | — | — | 10.0 | 5.0 | — |
| (16) Comparative compound (c1) | — | — | — | — | — | — | 1.0 | — | — | 0.1 |
| (17) Comparative compound (c2) | — | — | — | — | — | — | — | — | — | 0.1 |
| (18) Xanthan gum | 0.05 | 0.02 | 0.01 | — | 0.02 | 0.05 | 0.02 | 0.01 | — | 0.02 |
| (19) Potassium hydroxide | 0.03 | 0.01 | 0.05 | 0.1 | 0.01 | 0.03 | 0.01 | 0.05 | 0.1 | 0.01 |
| (20) Polyether modified silicone (*1) | 0.1 | 0.3 | 0.5 | 0.4 | 0.2 | 0.1 | — | 0.5 | 0.4 | 0.2 |
| (21) Methyl trimethicone (*2) | 4.0 | 4.0 | 4.0 | 4.0 | 4.0 | 4.0 | 4.0 | 4.0 | 4.0 | 4.0 |
| (22) Cetyl 2-ethylhexanoate | 3.0 | 3.0 | 3.0 | 3.0 | 3.0 | 3.0 | 3.0 | 3.0 | 3.0 | 3.0 |
| (23) Betaine lauryl acetate | 0.2 | 0.2 | 0.2 | 0.2 | 0.2 | 0.2 | 0.2 | 0.2 | 0.2 | 0.2 |
| (24) Isostearic acid | 0.15 | 0.15 | 0.15 | 0.15 | 0.15 | 0.15 | 0.15 | 0.15 | 0.15 | 0.15 |
| (25) Edetate | 0.02 | 0.1 | 0.01 | 0.06 | 0.1 | 0.02 | 0.1 | 0.01 | 0.06 | 0.1 |
| (26) Phenoxyethanol | 0.5 | 0.5 | 0.5 | 0.5 | 0.5 | 0.5 | 0.5 | 0.5 | 0.5 | 0.5 |
| (27) Perfume | 0.1 | 0.1 | 0.1 | 0.1 | 0.1 | 0.1 | 0.1 | 0.1 | 0.1 | 0.1 |
| Viscosity (mPa·s/25° C.) | 2500 | 4700 | 7500 | 5900 | 9300 | 5200 | 7400 | 5700 | 9500 | 13900 |
| White turbidity (L value) | 35 | 27 | 23 | 22 | 19 | 34 | 43 | 56 | 61 | 43 |
| Stability 0° C. | A | A | A | A | A | A | A | A | B | A |
| 25° C. | A | A | A | A | A | A | A | B | C | A |
| 30° C. | A | A | A | A | A | A | A | C | C | A |
| Dewy, watery feeling when applied | A | A | A | A | A | C | D | D | B | C |
| No stickiness | A | A | A | A | A | C | C | D | B | C |
| Refreshing feeling | A | A | A | A | A | C | C | D | B | D |
| Emollient feeling | A | B | A | A | B | B | C | B | D | C |

In Table 1, as "polyether modified silicone (*1)," "KF-6017P" (manufactured by Shin-Etsu Chemical Co., Ltd.; PEG-10 DIMETHICONE (INCI name)) was used. In addition, as "methyl trimethicone (*2)," "TMF-1.5 (product name)" (manufactured by Shin-Etsu Chemical Co., Ltd.; a viscosity at 25° C. of 1.5 mPa·s; METHYL TRIMETHICONE (INCI name)) was used.

The oil-in-water emulsified milky skin cosmetic preparation of the present invention is characterized in that it exhibits both the effect of a skin lotion and the effect of a skin milk. Accordingly, in order to be easily used as a skin lotion with good water texture, it is desired for the skin cosmetic preparation to be a composition having a relatively low viscosity. As is apparent from the results as shown in Table 1, the oil-in-water emulsified milky skin cosmetic preparations of Examples 1 to 5 were excellent in terms of dewy, watery feeling, no stickiness, a refreshing effect and an emollient feeling felt when applied, as well as stability and the degree of white turbidity. In particular, even a composition having a relatively low viscosity, like Example 1, maintained good stability. On the other hand, the oil-in-water emulsified milky skin cosmetic preparations of Comparative examples 1 to 5 were poor in terms of temperature stability and usability, and thus they did not sufficiently exhibit both the effect of a skin lotion and the effect of a skin milk, which is the object of the present invention.

The aforementioned results demonstrate that the oil-in-water emulsified milky skin cosmetic preparation of the present invention exhibits both the effect of a skin lotion and the effect of a skin milk.

Formulation examples will be further described below.

Example 6

| (Ingredients) | (mass %) |
|---|---|
| (1) Ion exchanged water | Balance |
| (2) Ethanol | 3.0 |
| (3) Glycerin | 3.0 |
| (4) Dipropylene glycol | 2.0 |
| (5) 1,3-butylene glycol | 2.0 |
| (6) Compound (c3) | 2.0 |
| (7) Compound (b1) | 0.05 |
| (8) Polymer (a2) | 0.5 |
| (9) Hydroxyethyl cellulose | 0.01 |
| (10) Sodium hydroxide | 0.01 |
| (11) Tranexamic acid | 2.0 |
| (12) Potassium 4-methoxysalicylate | 1.0 |
| (13) PEG-9 methyl ether dimethicone ("KF-6016"; manufactured by Shin-Etsu Chemical Co., Ltd.) | 0.1 |
| (14) Decamethyl cyclopentasiloxane | 4.0 |
| (15) 2-ethylhexyl 2-ethylhexanoate | 2.0 |
| (16) 1-piperidinepropionic acid | 0.1 |
| (17) Saxifraga extract | 0.01 |
| (18) Edetate | 0.02 |
| (19) Paraben | 0.1 |
| (20) Phenoxyethanol | 0.3 |
| (21) Perfume | 0.1 |

<Production Method>

While a aqueous phase, in which ingredients (1) to (12) and (16) to (20) had been uniformly dissolved, was stirred with a homomixer, an oil phase consisting of ingredients (13) to (15) and (21) was gradually added to the aqueous phase and was then emulsified, so as to obtain an oil-in-water emulsified milky skin cosmetic preparation.

Example 7

| (Ingredients) | (mass %) |
|---|---|
| (1) Ion exchanged water | Balance |
| (2) Ethanol | 3.0 |
| (3) Glycerin | 5.0 |
| (4) 1,3-butylene glycol | 2.0 |
| (5) Erythritol | 0.1 |

19
-continued

| (Ingredients) | (mass %) |
|---|---|
| (6) Compound (c1) | 5.0 |
| (7) Compound (b1) | 0.02 |
| (8) Polymer (a3) | 0.3 |
| (9) Hydroxyethyl cellulose | 0.01 |
| (10) Potassium hydroxide | 0.1 |
| (11) Ascorbic acid glucoside | 2.0 |
| (12) Potassium 4-methoxysalicylate | 1.0 |
| (13) Polyoxyethylene 60 mole-added hydrogenated castor oil | 0.1 |
| (14) Dimethyl polysiloxane ("KF-96A-6cs"; manufactured by Shin-Etsu Chemical Co., Ltd.) | 3.0 |
| (15) 2-ethylhexyl 2-ethylhexanoate | 2.0 |
| (16) Hydrolyzed wheat protein | 0.01 |
| (17) Rose apple leaf extract | 0.01 |
| (18) Edetate | 0.01 |
| (19) Paraben | 0.1 |
| (20) Phenoxyethanol | 0.3 |
| (21) Perfume | 0.1 |

<Production Method>

While a aqueous phase, in which ingredients (1) to (12) and (16) to (20) had been uniformly dissolved, was stirred with a homomixer, an oil phase consisting of ingredients (13) to (15) and (21) was gradually added to the aqueous phase and was then emulsified, so as to obtain an oil-in-water emulsified milky skin cosmetic preparation.

Example 8

| (Ingredients) | (mass %) |
|---|---|
| (1) Ion exchanged water | Balance |
| (2) Ethanol | 3.0 |
| (3) Glycerin | 4.0 |
| (4) 1,3-butylene glycol | 5.0 |
| (5) Xylitol | 0.5 |
| (6) Compound (c2) | 1.0 |
| (7) Compound (b1) | 0.02 |
| (8) Polymer (a3) | 0.3 |
| (9) Xanthan gum | 0.01 |
| (10) Potassium hydroxide | 0.1 |
| (11) Ethyl ascorbate | 0.5 |
| (12) Potassium 4-methoxysalicylate | 1.0 |
| (13) PEG-3 dimethicone ("KF-6015"; manufactured by Shin-Etsu Chemical Co., Ltd.) | 0.1 |
| (14) Dimethyl polysiloxane ("KF-96A-20cs"; manufactured by Shin-Etsu Chemical Co., Ltd.) | 1.0 |
| (15) Isotridecyl isononanoate | 5.0 |
| (16) Hydrolyzed wheat protein | 0.01 |
| (17) Rose apple leaf extract | 0.01 |
| (18) Edetate | 0.01 |
| (19) Paraben | 0.1 |
| (20) Phenoxyethanol | 0.3 |
| (21) Perfume | 0.1 |

<Production Method>

While a aqueous phase, in which ingredients (1) to (12) and (16) to (20) had been uniformly dissolved, was stirred with a homomixer, an oil phase consisting of ingredients (13) to (15) and (21) was gradually added to the aqueous phase and was then emulsified, so as to obtain an oil-in-water emulsified milky skin cosmetic preparation.

20

Example 9

| (Ingredients) | (mass %) |
|---|---|
| (1) Ion exchanged water | Balance |
| (2) Ethanol | 10.0 |
| (3) Glycerin | 7.0 |
| (4) Dipropylene glycol | 2.0 |
| (5) 1,3-butylene glycol | 1.0 |
| (6) Erythritol | 1.0 |
| (7) Polymer (a5) | 1.2 |
| (8) Compound (b2) | 0.02 |
| (9) Compound (c3) | 7.0 |
| (10) Hydroxyethyl cellulose | 0.01 |
| (11) Sodium hydroxide | 0.15 |
| (12) Tranexamic acid | 2.0 |
| (13) Ascorbic acid glucoside | 0.1 |
| (14) PEG-12 dimethicone ("SH3773M"; manufactured by TORAY Dow Corning Corp.) | 0.2 |
| (15) Dimethyl polysiloxane ("SH200 C Fluid-1cs"; manufactured by TORAY Dow Corning Corp) | 1.0 |
| (16) 2-ethylhexyl isononanoate | 2.0 |
| (17) Green tea extract | 0.01 |
| (18) Safflower extract | 0.01 |
| (19) Edetate | 0.01 |
| (20) Paraben | 0.1 |
| (21) Phenoxyethanol | 0.3 |
| (22) Perfume | 0.1 |

<Production Method and Evaluation>

While a aqueous phase, in which ingredients (1) to (13) and (17) to (21) had been uniformly dissolved, was stirred with a homomixer, an oil phase consisting of ingredients (14) to (16) and (22) was gradually added to the aqueous phase and was then emulsified, so as to obtain an oil-in-water emulsified milky skin cosmetic preparation.

What is claimed is:

1. An oil-in-water emulsified milky skin cosmetic preparation comprising the following ingredient (a), ingredient (b) and ingredient (c), and having a viscosity at 25° C. of 10,000 mPa·s or less (Vismetron viscometer), ingredient (a): a copolymer of 2-acrylamide 2-methylpropanesulfonic acid or a salt thereof/polyoxyethylene alkyl ether methacrylate represented by the following formula (I):

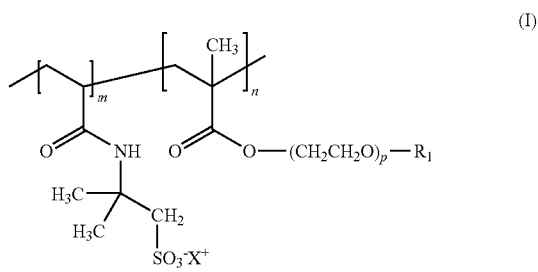

wherein each of m, n and p represents an average number of moles added, and m/n=4 to 99 and p represents an integer of 10 to 50; $X^+$ represents a proton, an alkaline metal cation, an alkaline-earth metal cation, ammonium ion, or an organic cation; $R_1$ represents a hydrogen atom, or a linear or branched alkyl group containing 5 to 40 carbon atoms;

ingredient (b): acrylates/$C_{10}$-$C_{30}$ alkyl acrylate crosspolymer; and ingredient (c): an alkylene oxide derivative represented by the following formula (II):

$$R_2O\text{-}[(AO)_a(EO)_b]\text{---}R_3 \qquad (II)$$

wherein AO represents an oxyalkylene group containing 3 or 4 carbon atoms; EO represents an oxyethylene group; each of a and b is an average number of moles added of the AO and EO, respectively, and $1 \leq a \leq 70$ and $1 \leq b \leq 70$; the percentage of EO to the sum of AO and EO [EO/(AO+EO)] is 20% to 80% by mass; and each of $R_2$ and $R_3$ independently represents an alkyl group containing 1 to 4 carbon atoms, wherein the composition comprises 0.005% to 2.0% by mass of the ingredient (a), 0.005% to 1.5% by mass of the ingredient (b), and 0.005% to 15.0% by mass of the ingredient (c).

2. The oil-in-water emulsified milky skin cosmetic preparation according to claim 1, which comprises oil having a viscosity at 25° C. of 100 mPa·s or less and being liquid state at an ordinary temperature, as ingredient (d).

3. The oil-in-water emulsified milky skin cosmetic preparation according to claim 2, which comprises 1.0% to 10.0% by mass of the ingredient (d).

4. The oil-in-water emulsified milky skin cosmetic preparation according to claim 1, which comprises 55% to 80% by mass of water.

5. The oil-in-water emulsified milky skin cosmetic preparation according to claim 1, the ingredient (a) is a crosscopolymer of 2-acrylamide 2-methylpropanesulfonic acid or a salt thereof/polyoxyethylene alkyl ether methacrylate.

* * * * *